United States Patent [19]

Nychka et al.

[11] 4,377,715
[45] Mar. 22, 1983

[54] PRODUCTION OF PERFLUOROPROPANE

[75] Inventors: Henry R. Nychka, East Aurora; John B. Hino, Cheektowaga; Richard E. Eibeck, Orchard Park; Martin A. Robinson, East Amherst, all of N.Y.

[73] Assignee: Allied Corporation, Morristown, N.J.

[21] Appl. No.: 107,123

[22] Filed: Dec. 26, 1979

[51] Int. Cl.$^3$ .................................... C07C 17/02
[52] U.S. Cl. .................................... 570/123; 570/175
[58] Field of Search .............. 260/653.9; 570/123, 570/175

[56] References Cited

U.S. PATENT DOCUMENTS

| | | | |
|---|---|---|---|
| 2,570,435 | 10/1951 | Downing et al. | 260/653.9 |
| 3,840,445 | 10/1974 | Paul et al. | 204/59 F |
| 4,158,023 | 6/1969 | von Halasz | 260/653.9 |
| 4,187,253 | 2/1980 | Kurtz | 260/662 R |

FOREIGN PATENT DOCUMENTS 990738  6/1976  Canada .................... 260/662 R

OTHER PUBLICATIONS

Maxwell et al., JACS 82, 5827–5830 (1960).

*Primary Examiner*—Charles F. Warren
*Assistant Examiner*—Joseph A. Boska
*Attorney, Agent, or Firm*—Thomas D. Hoffman; Alan M. Doernberg; Jay P. Friedenson

[57] ABSTRACT

Octafluoropropane or perfluoropropane is produced by introducing fluorine into an elongated inner zone surrounded by a porous member which is substantially resistant to fluorine corrosion and introducing a three carbon compound which is propane, a partially fluorinated propane, propene, a partially fluorinated propene, hexafluoropropene or mixtures thereof outside the porous member. When the porous member is metal, a perfluorinated diluent is used. When the porous member is fused alumina, conventional diluents such as nitrogen, or even no diluent may be employed.

10 Claims, No Drawings

PRODUCTION OF PERFLUOROPROPANE

BACKGROUND OF THE INVENTION

The present invention relates to the production of perfluoropropane or octafluoropropane which is known to be useful in plasma etching of electronic components and is a dielectric gas.

The production of perfluoropropane has been attempted from a variety of starting materials, but no process has been developed which produces the material in high yields without a multitude of steps. Exemplary starting materials are propane, propene, hexafluoropropene and partially halogenated propanes and propenes.

U.S. Pat. No. 4,158,023 to von Halasz describes the production of perfluoropropane from hexafluoropropene in two steps. This reference indicates that the direct conversion with elemental fluorine results in poor yields. Since hexfluoropropene is itself fairly hard to produce in good yields, the overall process becomes involved with a multitude of steps and expense.

U.S. Pat. No. 3,840,445 to Paul et al. describes electrochemical fluorination of propane to perfluoropropane. The reference indicates the difficulty in separating propane from the product by distillation, and, accordingly, employs a two-step process of electrochemical fluorination. Although the product need be separated only from partially fluorinated propane when the two steps are used, the process thereby becomes more involved, and the potential for overall yield losses increases.

The production of perfluoropropane from propane by elemental fluorination in a jet reactor has been described in an article by A. F. Maxwell et al. in *Journal of the American Chemical Society*, Vol. 82, pp. 5827–30 (Nov. 20, 1960). The tables in this article report production of perfluoropropane which suggests a yield, in the best case, of about 50 percent based on propane fed.

Porous tube fluorinations are described in two applications filed herewith, which are not admitted to constitute prior art with respect to the present application. In the first application having the same inventorship as the present application Ser. No. 107,124 filed Dec. 26, 1979, fluorine-resistant fused alumina tubes are used for elemental fluorination of a variety of organic materials. In the other application having an additional coinventor Ser. No. 107,122 filed Dec. 26, 1979, a metal tube is used together with a perfluorinated diluent. Such applications describe a variety of details concerning suitable and preferred diluents, configurations, organic starting materials and other conditions suitable for the general reaction of organics with fluorine in such a reactor. The present invention is based upon the surprisingly good yields of perfluoropropane in either type of reactor from such diverse materials as propane, propene, and hexafluoropropene. Such results are believed to constitute an invention separate and apart from the more general application of either reaction to elemental fluorinations for a variety of materials, especially in view of the difficulties in producing perfluoropropane evidenced by the above-cited prior art.

A previous disclosure of Kurtz described in Canadian Pat. No. 990,738 and also in pending U.S. application Ser. No. 644,788, filed Dec. 29, 1975, commonly assigned now U.S. Pat. No. 4,187,253 issued Feb. 5, 1980, involves the chlorination of organics in similar reactors. Unlike the present fluorinations, chlorinations reported in Kurtz's disclosure appear to produce only partial chlorination of alkanes of more than one carbon.

BRIEF DESCRIPTION OF THE INVENTION

The present invention includes a method of preparing octafluoropropane which comprises:

(a) introducing a first gaseous reactant stream comprising fluorine into an elongated inner zone surrounded by porous member which is substantially resistant to fluorine corrosion;

(b) introducing a second gaseous reactant stream outside the porous member comprising a three carbon compound selected from the group consisting of propane, partially fluorinated propanes, propene, partially fluorinated propenes, hexafluoropropene and mixtures thereof; and (c) recovering octafluoropropane from the effluent outside the porous member;

the pressure in the elongated inner zone being greater than the pressure outside the porous member.

Preferred three carbon compounds are propane, propene and hexafluoropropene.

DETAILED DESCRIPTION OF THE INVENTION

The porous member or porous tube used for the reactor in the present invention may be of any material resistant to fluorine corrosion which has pores of relatively small diameter, such as between about 1 and about 100 micrometers and which retains its structure and pore configuration under the present reaction conditions. Fluorine is introduced into the interior of the porous member or into the elongated inner zone. The fluorine may be introduced by itself or together with a diluent such as nitrogen, sulfur hexafluoride, helium, the byproduct HF, recycled product perfluoropropane or other inert gases. A second gaseous reactant stream comprising the three carbon compound or organic is introduced outside the porous member, preferably in an annular zone between the porous member and a surrounding impervious member. The pressure in the elongated inner zone should be greater than that outside the porous member so that the fluorine will migrate outwardly through the porous member and so as to prevent back migration of organics inwardly through the porous member. At the outer surface of the porous member, the fluorine reacts with the organic or three carbon compound to produce three carbon compounds having a higher fluorine content and, especially, perfluoropropane.

While a diluent is preferred to be present, they are required, or at least appear to be required, when the porous member is metal such as copper, nickel or the like. For the present invention, however, it is not intended that any limitation be necessarily placed on the reaction with regard to diluents since, with sufficient dilution or other temperature control, it is believed that perfluoropropane can be made even with conventional diluents such as nitrogen in a metal porous tube. It is recognized, however, that experiments with compounds such as ethane as the organic have led to high levels of cleavage where a perfluorinated diluent was absent and a metal porous tube was used.

Accordingly, the preferred porous tube for the present reaction is that formed of fused alumina, heated at a temperature sufficient to make the porous member resistant to fluorine corrosion. The preferred three carbon compounds are propane, propene and hexafluoropropene, and especially preferred is propane.

Where propane is the reactant, octafluoropropane can be recovered from the effluent by condensing the effluent under sufficiently high pressure and low temperature to condense octafluoropropane, separating the condensate from the uncondensed portion of the effluent, separating an organic phase of the condensate from a hydrogen fluoride phase of the condensate and recovering octafluoropropane from the organic phase of the condensate. The preferred method of recovering octafluoropropane from the organic phase of the condensate is by fractional distillation since, once phase separation has occurred, no compounds boiling close to octafluoropropane will remain in the condensate. It should be appreciated that, if propane itself were present in the effluent, it would also be found in the organic phase of the condensate and would, according to U.S. Pat. No. 3,840,445 complicate purification. In the examples described below having a stoichiometric excess of fluorine, no propane was detected in the effluent and no difficulty should be encountered in separating perfluoropropane from other materials by fractional distillation.

The ratio of fluorine to three carbon compound depends, in part, upon the particular three carbon compound employed. Thus, in general, one can compute the stoichiometric amount of fluorine required to convert the entire second reactant to a perfluoropropane as a first estimate of the desired amount of fluorine to be introduced.

For coupounds having a hydrogen, one mole of fluorine is required for each mole of hydrogen bonded to carbon such that half of the fluorine molecule can replace the hydrogen to form a C-F bond and the other half of the fluorine molecule can form HF by-product. For each unsaturation, one mole of fluorine is required to add across a double bond and to form two C-F bonds. For each other halogen present such as Cl or Br, or any other hetero atom present, one molecule of fluorine is generally required to both replace the hetero atom and form a by-product between fluorine and the hetero atom. In general, however, hetero atoms are preferably not present such that the three carbon compound has no elements other than carbon, hydrogen and fluorine.

While any amount of fluorine may be used, it is preferred to use between 50 and 150 percent of the stoichiometric amount. Thus, in the case of propane, 8 moles of fluorine per propane constitutes the stoichiometric amount, and a generally suitable range of fluorine is between about 4 and about 12 moles of fluorine per propane. Preferably, between about 5 and about 10 moles of fluorine are introduced into the inner zone per mole of propane introduced outside the elongated porous member. More preferably between about 8 and about 9.5 moles of fluorine are introduced per mole of fluorine.

In the case of propene, the stoichiometric amount is 7 moles of fluorine per propene. A generally suitable overall range is between about 3.5 and about 10.5 moles of fluorine per mole of propene. A preferred range of fluorine to propene ratios is between about 4:1 and about 8:1, more preferably between about 7:1 and about 8:1.

In the use of hexafluoropropene, the stoichiometric mole ratio is 1:1 while a range of about 0.5:1 to about 1.5:1 is suitable, as well as amounts higher, and especially lower in fluorine than that range, the preferred ratios are between about 0.7:1 and about 1.1:1, especially about 1:1.

EXAMPLE 1

Fluorine (0.53 mol/h) and helium (0.25 mol/h) were introduced into a porous tube 15.2 cm (6 inches) in height and 1.9 cm (0.75 inches) in diameter. Propane (0.060 mol/h) was introduced into the base of an annular zone between the outside of the porous member and an outer impervious stainless steel tube. The overall configuration was such that the inner zone of diameter was surrounded by a wall thickness of 0.6 cm (0.25 inches) which in turn was surrounded by an annulus of 0.95 cm (0.375 inches). The pressure inside the porous tube was maintained slightly above the pressure outside the porous tube. Product was withdrawn from the top of the impervious tube, above the upper end of the porous tube. The porous tube was of fused alumina having a porosity (ratio of void space to total volume) of 21%, permeability (mL of air/min. through a piece of one inch thick and one square inch in area with a pressure differential of one inch of water) between 12 and 20 and a chemical analysis of 99.5% $Al_2O_3$, 0.07% $SiO_2$, 0.09% $Fe_2O_3$ and 0.25% $K_2O$ and $Na_2O$ (sold by the Norton Company of Worchester, Massachussets as ALUNDUM AN-299A fused alumina, "ALUNDUM" being their registered trademark). The total product was condensed in a liquid nitrogen chilled trap and analyzed by gas chromatography. Prior to condensation, HF was removed from the effluent by scrubbing with NaF. In a six-hour experiment 122 grams of fluorine and 15.9 grams of propane were fed, for a total of 137.8 grams of reactants fed in. Product recovery was 60 grams HF and 73.4 grams of organic product, for a total of 133.4 grams or a 97 percent mass recovery. Gas chromatography analysis of the organic indicated 2.4 weight percent carbon tetrafluoride, 2.0 percent carbon dioxide, 4.6 percent perfluoroethane, 68.4 percent perfluoropropane, 21.6 percent other three and six carbon fluorinated alkanes and 1.0 percent unknowns. Thus, based solely on the 68.4 percent of the 73.4 grams product, the yield per pass was 73 percent based on propane fed. It should be appreciated that at least a portion of the 21.6 percent was also materials such as partially fluorinated propane which could, if recycled, produce additional perfluoropropane.

EXAMPLES 2-17

Fluorinations of Propane and Propene in Fused Alumina Porous Tube

Using the porous tube of Example 1, a number of experiments were performed feeding the mol/h of fluorine and mol/h of diluent (either sulfur hexafluoride or nitrogen) into the interior of the porous tube indicated in Table 1 under the heading "Inner Zone". In addition, the amounts of propane and diluent indicated in Table 1 under the heading "Outer Zone" were fed into the annular space around the porous tube. The maximum temperature along the outside of the porous tube was monitored with a thermowell and is indicated in Table 1. Contact times computed from reactant flow rates, reaction temperatures and volume of annulus are also indicated in Table 1. Gas chromatographic analysis of the effluent after absorption of HF by NaF was performed and the results compared to control samples so as to calculate a yield of octafluorpropane based on fluorine in cases where less fluorine than the stoichiometric amount was introduced and based on propane fed where less than the stoichiometric amount of propane was introduced. In Table 1 the fluorination ratio or "F. Rat." is shown to indicate the mole ratio of fluorine to propane or propene which should be compared to the stoichiometric amount which is 8 in the case of propane and 7 in the case of propene. The yields reported in Table 1 do not take into account partially fluorinated propanes and propenes which could be converted to additional octafluoropropane if recycled.

TABLE 1

Fluorinations of Propane and Propene In Fused Alumina Porous Tube

| Ex. | F.Rat. | Outer Zone | | Inner Zone | | Max. Temp. | CT Sec. | Yield $C_3F_8$ |
|---|---|---|---|---|---|---|---|---|
| | | Propane | $SF_6$ | $F_2$ | $SF_6$ | | | |
| 2 | 1 | 0.25 | 0.50 | 0.25 | 2.0 | 96° C. | 9 | nil |
| 3 | 3 | 0.25 | 0.50 | 0.75 | 2.0 | 210 | 8 | 10 |
| 4 | 1 | 0.25 | 0 | 0.25 | 0.25 | 63 | 37 | 55 |
| 5 | 2 | 0.25 | 0 | 0.50 | 0.25 | 93 | 28 | 47 |
| 6 | 3 | 0.25 | 0 | 0.75 | 0.50 | 252 | 18 | 33 |
| 7 | 9.5 | 0.063 | 0 | 0.60 | 0.50 | 222 | 24 | 71 |
| 7A | 9.5 | 0.063 | 0 | 0.60 | 0.25 | 210 | 30 | 72 |
| | | Propane | $N_2$ | $F_2$ | $N_2$ | | | |
| 8 | 9.5 | 0.063 | 0 | 0.60 | 1.0 | 219 | 17 | 65 |
| 9 | 9.5 | 0.063 | 0 | 0.60 | 0.5 | 232 | 23 | 74 |
| 10 | 9.5 | 0.063 | 0 | 0.60 | 0.25 | 234 | 30 | 73 |
| 11 | 9.5 | 0.063 | 0 | 0.60 | 0 | 233 | 42 | 85 |
| | | Propene | $N_2$ | $F_2$ | $N_2$ | | | |
| 12 | 8.3 | 0.072 | 0 | 0.60 | 1.0 | 230 | 17 | 37 |
| 13 | 8.3 | 0.072 | 0 | 0.60 | 0.5 | 238 | 24 | 44 |
| 14 | 8.3 | 0.072 | 0 | 0.60 | 0.25 | 238 | 30 | 50 |
| 15 | 8.3 | 0.072 | 0 | 0.60 | 0 | 235 | 40 | 35 |
| 16 | 7.0 | 0.086 | 0 | 0.60 | 0 | 221 | 30 | 45 |
| | | Propene | $SF_6$ | $F_2$ | $SF_6$ | | | |
| 17 | 8.3 | 0.072 | 0 | 0.60 | 0.25 | 236 | 30 | 40 |

EXAMPLES 18-21

Fluorination of Propane and Propene in Metal Porous Tubes

Examples 2-17 were repeated using a similar apparatus, but with a tube of Inconel (a nickel-iron-chromium alloy) having a height of 15.2 cm (6 inches), 3.8 cm diameter (1.5 inches), 0.165 cm (0.0625 inches) wall thickness and 20 micrometer pore size. The feeds were 0.25 or 0.50 mol/h of $F_2$ admixed with 2.0 mol/h of $SF_6$ into the bottom of the porous tube and 0.25 mol/h of propane or propene admixed with 0.50 mol/h of $SF_6$ into the annular zone, all as shown in Table 2. On-line gas chromatographic analysis of the vaporized effluent gave the area percentages which were converted into yield of perfluoropropane as shown.

TABLE 2

Fluorination of C-3 Hydrocarbons

| Example Feeds | 18 propene | 19 propane | 20 propane | 21 propane |
|---|---|---|---|---|
| Outer zone C-3 Organic (0.25 mol/h) | | | | |
| $SF_6$ (mol/h) | 2.0 | 2.0 | 2.0 | 2.0 |
| inner zone | | | | |
| $F_2$ (mol/h) | 0.25 | 0.25 | 0.50 | 0.75 |
| $SF_6$ (mol/h) | 0.50 | 0.50 | 0.50 | 0.50 |
| $CF_4$ (area %) | 3 | 0 | 3 | 5 |
| $C_3F_8$ (area %) | 18 | 18 | 58 | 53 |
| $C_3H_{1-7}F_{7-1}$*(area %) | 79 | 82 | 39 | 42 |
| $C_3F_8$ yield | 18 | 17 | 54 | 49 |

TABLE 2-continued

Fluorination of C-3 Hydrocarbons

| Example Feeds | 18 propene | 19 propane | 20 propane | 21 propane |
|---|---|---|---|---|
| (based on $F_2$) | | | | |

*together with similar partially fluorinated hexanes

EXAMPLES 22-25

Fluorination of Hexafluoropropene in Porous Alumina Tube

Examples 2-17 were repeated with hexafluoropropene ("HFP") as the organic feed. These Examples illustrate the susceptability of double bonds as the sole "fluorinatable carbons" to fluorination by the present process. The feed rates, operating conditions and results are displayed in Table 3. The area % of nitrogen is included in the analysis (diluent was excluded in previous tables).

TABLE 3

Fluorination of Hexafluoropropene

| Ex. Organic | 22 HFP | 23 HFP | 24 HFP | 25 HFP |
|---|---|---|---|---|
| O.Z. Organic | 0.30 | 0.25 | 0.25 | 0.50 |
| I.Z. $F_2$ | 0.25 | 0.25 | 0.25 | 0.50 |
| I.Z. $N_2$ | 1.0 | 1.0 | 0.50 | 0.25 |
| Max. Temp. | 143° C. | 170° C. | 184° C. | 254° C. |
| Contact Time | 18 s | 18.5 s | 28 s | 22 s |
| GC Analysis (Area %): | | | | |
| $N_2$ | 57.8 | 60.8 | 46.4 | 19.3 |
| $CF_4, C_2F_6$ | 0.2 | 0.4 | 0.8 | 0.9 |
| $C_3F_6$ | 2.1 | 0 | 0 | 0 |
| $C_3F_8$ | 25.8 | 22.8 | 36.7 | 58.5 |
| $C_6F_{14}$ | 14.1 | 16.0 | 16.1 | 21.3 |
| % Yield $C_3F_8$ ($F_2$ basis) | 80 | 66 | 70 | 67 |

What is claimed is:
1. A method of preparing octafluoropropane which comprises:
 (a) introducing a first gaseous reactant stream comprising fluorine into an elongated inner zone surrounded by porous member which is substantially resistant to fluorine corrosion;
 (b) introducing a second gaseous reactant stream outside the porous member comprising a three carbon compound selected from the group consisting of propane, propene and mixtures thereof; and
 (c) recovering octafluoropropane from the effluent outside the porous member;
 the pressure in the elongated inner zone being greater than the pressure outside the porous member.
2. The method of claim 1 wherein the three carbon compound is propane and wherein said recovering step comprises condensing the effluent under sufficiently high pressure and low temperature to condense octafluoropropane, separating the condensate from the uncondensed portion of the effluent, separating an organic phase of the condensate and recovering octafluoropropane from the organic phase of the condensate.
3. The method of claim 2 wherein octafluoropropane is recovered from the organic phase of the condensate by fractional distillation.
4. The method of claim 1 wherein fluorine is introduced at between about 4 and 12 times the moles of propane.

5. The method of claim 4 wherein fluorine is introduced at between about 5 and about 10 times the moles of propane.

6. The method of claim 5 wherein fluorine is introduced at between about 8 and about 9.5 times the moles of propane.

7. the method of claim 1 wherein the three carbon compound is propene.

8. The method of claim 7 wherein fluorine is introduced at between about 3.5 and about 10.5 times the moles of propene.

9. The method of claim 8 wherein fluorine is introduced at between about 4 and about 8 times the moles of propene.

10. The method of claim 9 wherein fluorine is introduced at between about 7 and 8 times the moles of propene.

* * * * *